United States Patent
Do et al.

(10) Patent No.: US 9,539,417 B1
(45) Date of Patent: Jan. 10, 2017

(54) VACUUM ASSEMBLY

(71) Applicants: Christopher N. Do, San Jose, CA (US); Sabrina Do, San Jose, CA (US)

(72) Inventors: Christopher N. Do, San Jose, CA (US); Sabrina Do, San Jose, CA (US)

(*) Notice: Subject to any disclaimer, the term of this patent is extended or adjusted under 35 U.S.C. 154(b) by 578 days.

(21) Appl. No.: 14/042,785

(22) Filed: Oct. 1, 2013

(51) Int. Cl.
*A61M 31/00* (2006.01)
*A61M 1/00* (2006.01)

(52) U.S. Cl.
CPC ........... *A61M 31/00* (2013.01); *A61M 1/0031* (2013.01)

(58) Field of Classification Search
CPC A61M 1/0058; A61M 1/0031; A61M 1/0064; A61M 3/02; A61M 3/0279; A61M 3/0283; A61M 5/142
See application file for complete search history.

(56) References Cited

U.S. PATENT DOCUMENTS

| | | | |
|---|---|---|---|
| 474,269 A | 5/1892 | Silvey | |
| 536,781 A | 4/1895 | Draver | |
| 4,995,386 A | 2/1991 | Ng | |
| 5,098,386 A | 3/1992 | Smith | |
| 5,582,167 A * | 12/1996 | Joseph | A61M 16/0479 128/202.22 |
| 5,800,425 A | 9/1998 | DeLeonardis | |
| 6,135,980 A | 10/2000 | Vu | |
| 6,517,511 B2 | 2/2003 | Yao | |
| 6,595,949 B1 | 7/2003 | Shapiro | |
| 2005/0049620 A1 | 3/2005 | Chnag | |
| 2008/0312674 A1 | 12/2008 | Chen et al. | |
| 2011/0054389 A1* | 3/2011 | Do | A61M 1/0023 604/28 |
| 2012/0289894 A1* | 11/2012 | Douglas | A61M 1/0047 604/31 |

\* cited by examiner

*Primary Examiner* — Laura Bouchelle

(57) ABSTRACT

A vacuum assembly for clearing a user's nasal passage includes a housing that may be positioned proximate a user. A pump is coupled to the housing. A medication reservoir is coupled to the pump. The medication reservoir is operationally coupled to the pump. A port is coupled to the housing. The port is operationally coupled to an inlet of the pump. An actuator is coupled to the housing. The actuator actuates the pump. A control is coupled to the housing. The control adjusts a pressure of the pump. A meter is coupled to the housing. The meter displays a pressure of the pump. A tube is operationally coupled to the port. A canister is operationally coupled to the tube. A tip is operationally coupled to the tube. The tip is selectively inserted into the user's nasal passage so the user's nasal passage is cleared.

18 Claims, 4 Drawing Sheets

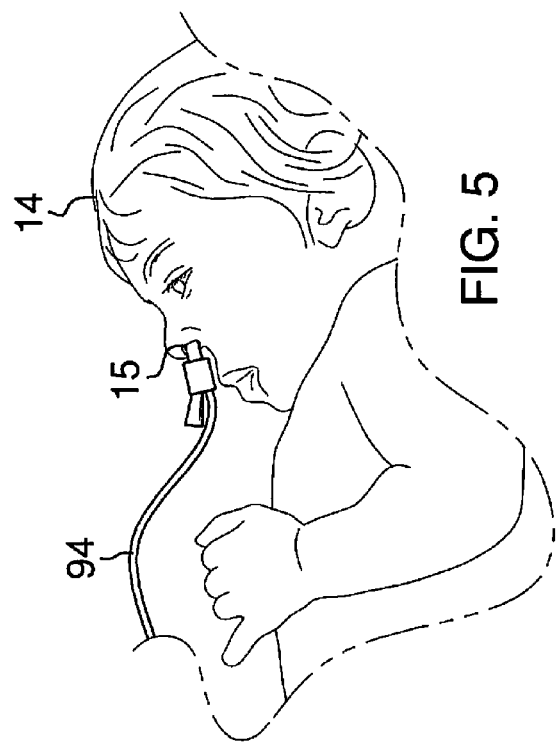
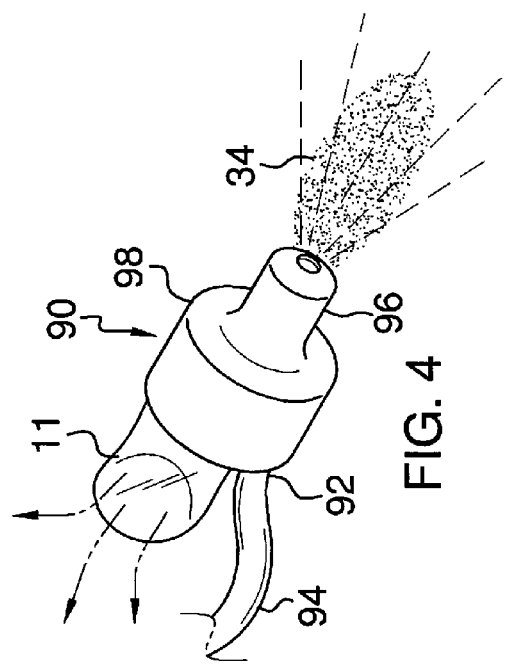

VACUUM ASSEMBLY

BACKGROUND OF THE DISCLOSURE

Field of the Disclosure

The disclosure relates to vacuum devices and more particularly pertains to a new vacuum device for clearing a user's nasal passage.

SUMMARY OF THE DISCLOSURE

An embodiment of the disclosure meets the needs presented above by generally comprising a housing that may be positioned proximate a user. A pump is coupled to the housing. A medication reservoir is coupled to the pump. The medication reservoir may selectively receive a medication. The medication reservoir is operationally coupled to the pump. The medication reservoir delivers the medication to the pump. A port is coupled to the housing. The port is operationally coupled to an inlet of the pump. An actuator is coupled to the housing. The actuator is operationally coupled to the pump so the actuator actuates the pump. A control is coupled to the housing. The control is operationally coupled to the pump so the control adjusts a pressure of the pump. A meter is coupled to the housing. The meter is operationally coupled to the pump so the meter displays a pressure of the pump. A tube is operationally coupled to the port. A canister is operationally coupled to the tube. A tip is operationally coupled to the tube. The tip is selectively inserted into the user's nasal passage so the user's nasal passage is cleared.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 4 is a perspective view of an embodiment of the disclosure.

FIG. 5 is an in-use view of an embodiment of the disclosure.

DESCRIPTION OF THE PREFERRED EMBODIMENT

Figure 1:
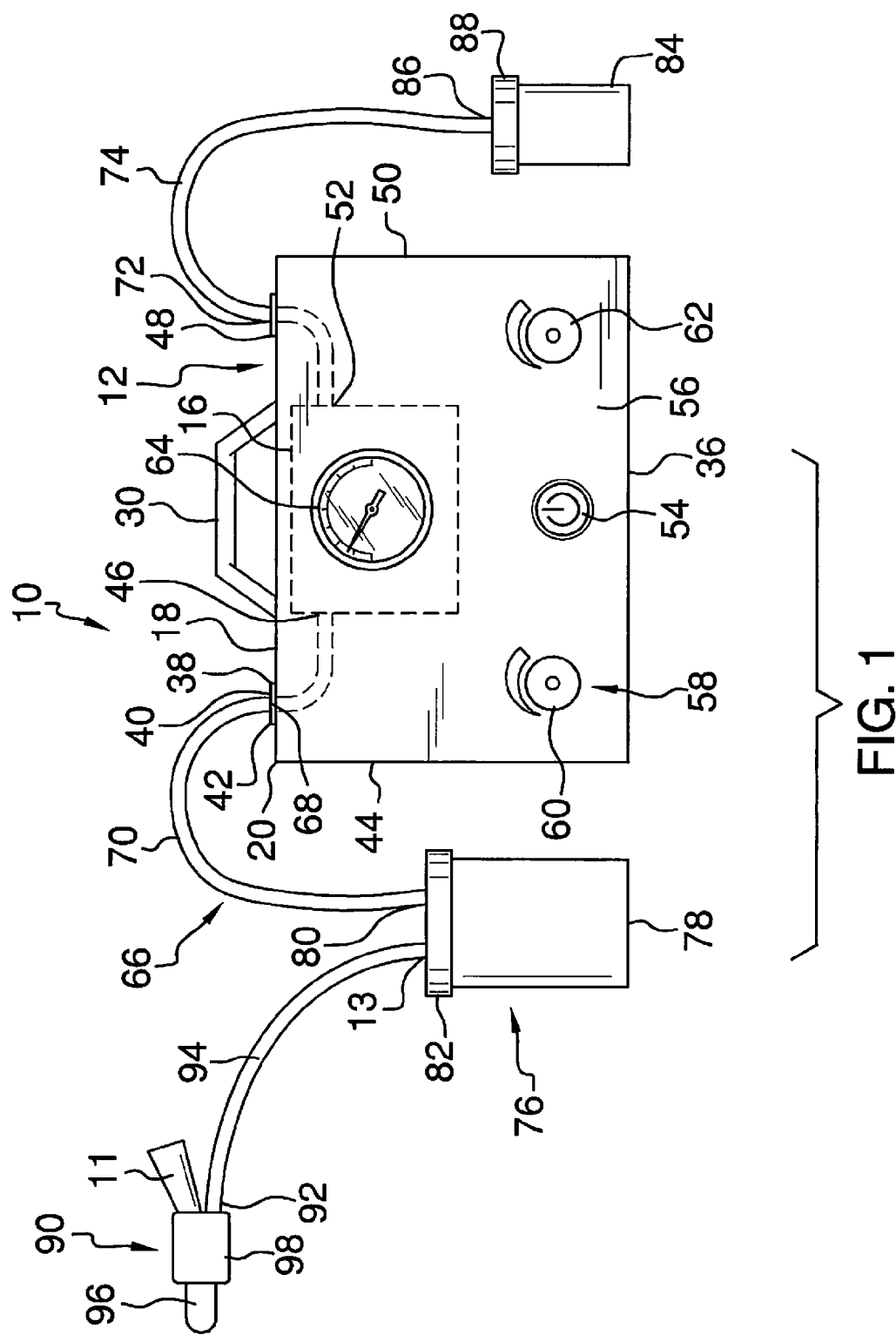
FIG. 1 is a front view of a vacuum assembly according to an embodiment of the disclosure.
Figure 3:
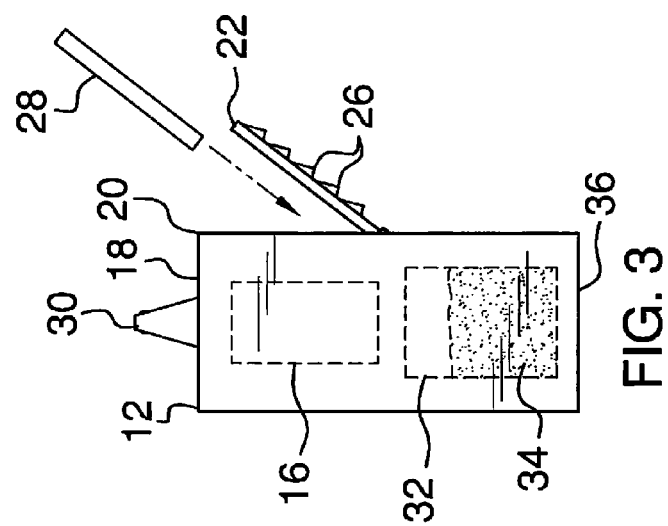
FIG. 3 is a left side view of an embodiment of the disclosure.
Figure 2:
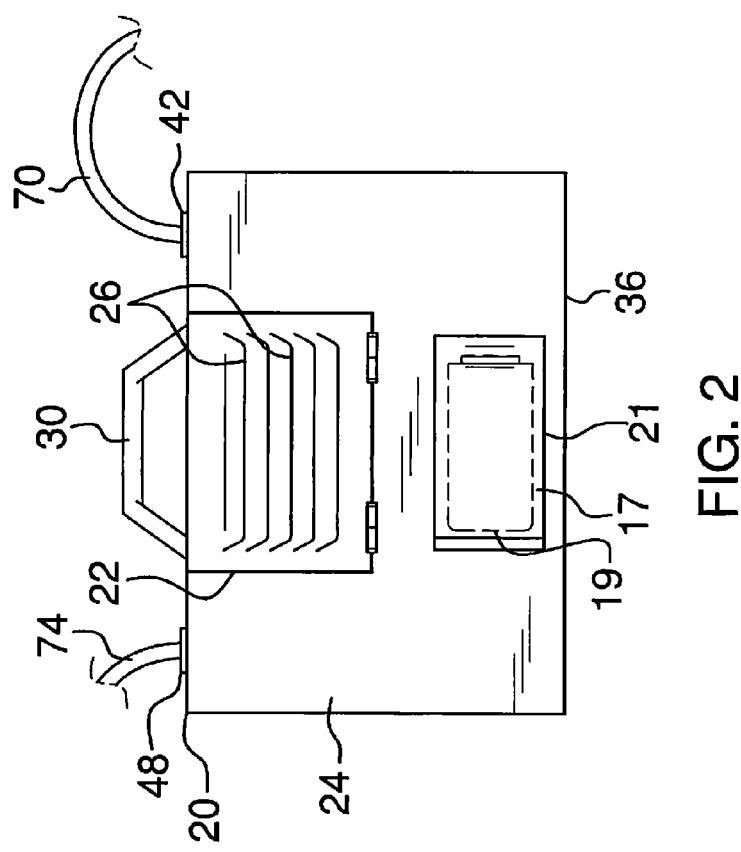
FIG. 2 is a back view of an embodiment of the disclosure.
Figure 6:
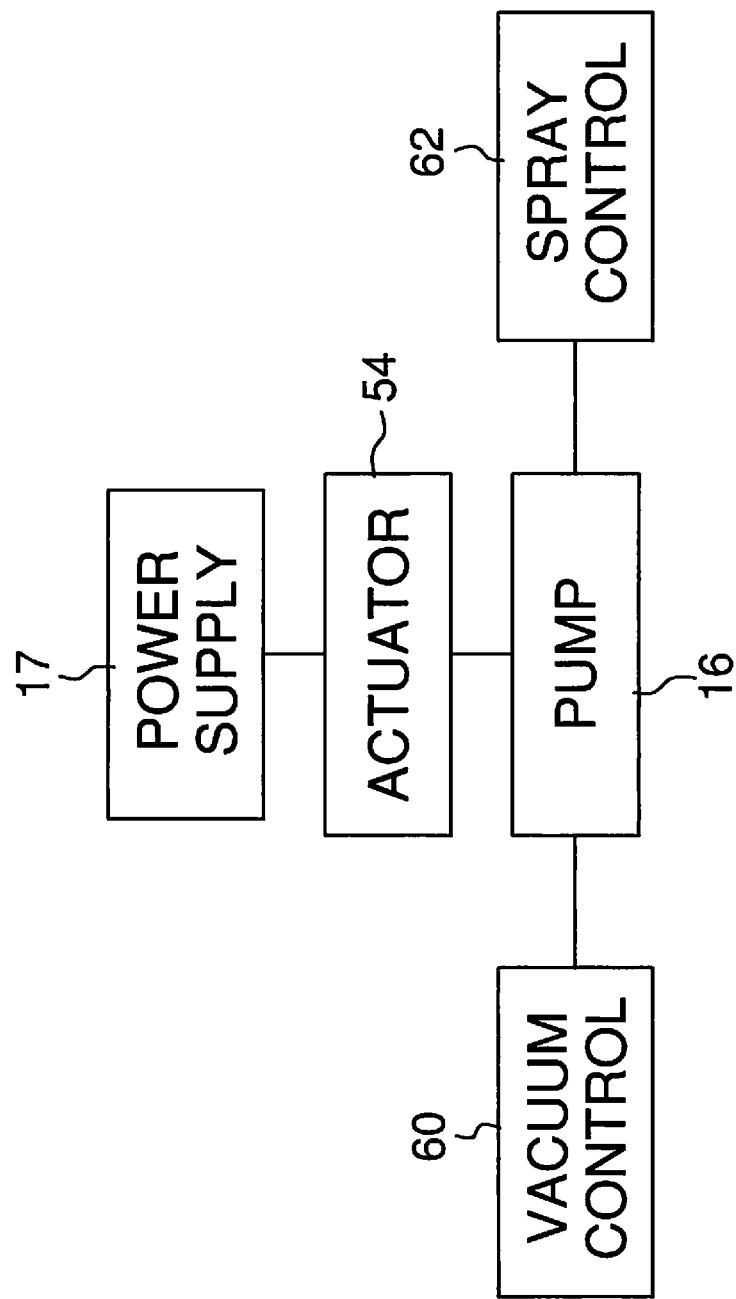
FIG. 6 is a schematic view of an embodiment of the disclosure.

With reference now to the drawings, and in particular to FIGS. 1 through 6 thereof, a new vacuum device embodying the principles and concepts of an embodiment of the disclosure and generally designated by the reference numeral 10 will be described.

As best illustrated in FIGS. 1 through 6, the vacuum assembly 10 generally comprises a housing 12 that may be positioned proximate a user 14. The user 14 may be a child. The housing 12 may have a length between 20 cm and 25 cm, a width between 15 cm and 20 cm and a height between 18 cm and 23 cm. A pump 16 is coupled to the housing 12. Moreover, the pump 16 is positioned within an interior of the housing 12 proximate a top side 18 of an outer wall 20 of the housing 12. The pump 16 may be an dual mode electric pump of any conventional design. Additionally, the pump 16 may generate a vacuum pressure between 0 inHg and 24 inHg. Lastly, the pump 16 may generate a spray pressure between 10 cmHg and 20 cmHg.

A door 22 is hingedly coupled to a back side 24 of the outer wall 20 of the housing 12 proximate the top side 18 of the outer wall 20 of the housing 12. A plurality of vents 26 extends through the door 22. Moreover, a filter 28 is positionable between the door 22 and the pump 16. The pump 16 draws air through the plurality of vents 26 in the door 22. Further, the filter 28 filters the air drawn through the plurality of vents 26. A handle 30 is coupled to the top side 18 of the outer wall 20 of the housing 12 so the housing 12 may be carried.

A medication reservoir 32 is coupled to the pump 16. The medication reservoir 32 may selectively receive a medication 34. Moreover, the medication reservoir 32 is positioned within an interior of the housing 12 proximate a bottom side 36 of the outer wall 20 of the housing 12. The medication reservoir 32 is in fluid communication with the pump 16 so the pump 16 draws the medication 34 outwardly from the medication reservoir 32. The medication 34 may be a liquid respiratory medication of any conventional design.

A port 38 is coupled to the top side 18 of the outer wall 20 of the housing 12. Further, a top 40 of the port 38 extends upwardly from the top side 18 of the outer wall 20 of the housing 12. The port 38 is fluidly coupled to the pump 16. Additionally, the port 38 is one of a pair of the ports 38.

A vacuum one of the pair of ports 42 is positioned proximate a first lateral side 44 of the outer wall 20 of the housing 12. The vacuum port 42 is fluidly coupled to an inlet 46 of the pump 16. Further, a spray one of the pair of ports 48 is positioned proximate a second lateral side 50 of the outer wall 20 of the housing 12. The spray port 48 is fluidly coupled to an outlet 52 of the pump 16. Moreover, each of the vacuum 42 and the spray 48 ports may have a diameter between 6 mm and 12 mm.

An actuator 54 is centrally coupled to a front side 56 of the outer wall 20 of the housing 12 proximate the bottom side 36 of the outer wall 20 of the housing 12. The actuator 54 is electrically coupled to the pump 16 so the actuator 54 selectively actuates and de-actuates the pump 16. A control 58 is rotatably coupled to the front side 56 of the outer wall 20 of the housing 12. Lastly, the control 58 is one of a pair of the controls 58.

A vacuum one of the pair of controls 60 is positioned proximate an intersection of the bottom side 36 and the first lateral side 44 of the outer wall 20 of the housing 12. The vacuum control 60 is operationally coupled to the inlet 46 of the pump 16. Moreover, the vacuum control 60 adjusts a vacuum pressure of the inlet 46 of the pump 16 between a minimum and a maximum pressure. A spray one of the pair of controls 62 is positioned proximate an intersection of the bottom side 36 and the second lateral side 50 of the outer wall 20 of the housing 12. The spray control 62 is operationally coupled to the outlet 52 of the pump 16. Lastly, the spray control 62 adjusts a spray pressure of the outlet 52 of the pump 16 between a minimum and a maximum pressure.

A meter 64 is centrally coupled to the front side 56 of the outer wall 20 of the housing 12 proximate the top side 18 of the outer wall 20 of the housing 12. The meter 64 is operationally coupled to the pump 16. Additionally, the meter 64 displays a operational pressure of the pump 16. Lastly, the meter 64 may be a pressure gauge of any conventional design.

A tube 66 is operationally coupled to the port 38. Further, the tube 66 is one of a pair of the tubes 66. A first end 68 of a vacuum one of the pair of tubes 70 is fluidly coupled to the vacuum port 42. Moreover, a first end 72 of a spray one of the pair of tubes 74 is fluidly coupled to the spray port 48. Each of the vacuum 70 and the spray 74 tubes may be flexible medical tubing of any conventional design.

A canister 76 is operationally coupled to the tube 66. Further, the canister 76 is one of a pair of the canisters 76. A vacuum one of the pair of canisters 78 is fluidly coupled to a second end 80 of the vacuum tube 70. Moreover, the vacuum tube 70 enters a removable top 82 of the vacuum canister 78. Continuing, a spray one of the pair of canisters 84 is fluidly coupled to a second end 86 of the spray tube 74. The spray tube 74 enters a removable top 88 of the spray canister 84 so the pump 16 delivers the medication into the spray canister 84.

A tip 90 is fluidly coupled to a second end 92 of a tip tube 94. The tip 90 includes a nozzle 96 extending forwardly from a coupling portion 98 of the tip 90. Further, an overflow 11 extends rearwardly from the coupling portion 98 of the tip 90. Moreover, the nozzle 96 and the overflow 11 are each in fluid communication with the tip tube 94.

A first end 13 of the tip tube 94 is selectively fluidly coupled to a selected one of the vacuum canister 78 or the spray canister 84 so the tip 90 produces a vacuum pressure or a spray pressure. The nozzle 96 is selectively inserted into the user's nasal passage 15. Moreover, the user's nasal passage 15 is cleared when the tip tube 94 is fluidly coupled to the vacuum canister 78. Further, the nozzle 96 delivers the medication 34 into the user's nasal passage 15 when the tip tube 94 is fluidly coupled to the spray canister 84.

A power supply 17 is coupled to the housing 12. Further, the power supply 17 is electrically coupled to the actuator 54. The power supply 17 comprises at least one battery 19. Moreover, the battery 19 is positioned beneath a battery cover 21. The battery cover 21 is positioned on the back side 24 of the outer wall 20 of the housing 12 proximate the bottom side 36 of the outer wall 20 of the housing 12.

In use, the tip tube 94 is coupled to the selected vacuum 78 or spray 84 canisters. The nozzle 96 is positioned in the user's nasal passage 15. When the vacuum canister 78 becomes full from clearing the user's nasal passage 15, the removable top 82 is removed and the vacuum canister 78 is emptied. The medication 34 is selectively placed in the medication reservoir 32 when the tip tube 94 is fluidly coupled to the spray canister 84. The nozzle 96 is positioned in the user's nasal passage 15 so the medication 34 is delivered into the user's nasal passage 15. Moreover, the vacuum 60 and spray 62 controls may be adjusted at any time during use.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:

1. A vacuum assembly for clearing a user's nasal passage, said assembly comprising:
   a housing configured to be positioned proximate the user;
   a pump coupled to said housing;
   a medication reservoir coupled to said pump wherein said medication reservoir is configured to selectively receive a medication, said medication reservoir being operationally coupled to said pump wherein said medication reservoir delivers the medication to said pump;
   a port coupled to said housing, said port being operationally coupled to an inlet of said pump;
   an actuator coupled to said housing, said actuator being operationally coupled to said pump wherein said actuator actuates said pump;
   a control coupled to said housing, said control being operationally coupled to said pump wherein said control adjusts a pressure of said pump;
   a meter coupled to said housing, said meter being operationally coupled to said pump wherein said meter displays a pressure of said pump;
   a tube operationally coupled to said port;
   a canister operationally coupled to said tube;
   a tip tube fluidly coupled to and extending from said canister;
   a tip operationally coupled to said tip tube wherein said tip is operationally coupled to said tube, said tip being selectively inserted into the user's nasal passage wherein the user's nasal passage is cleared, said tip including a nozzle and a coupling portion, said nozzle being configured for insertion into the user's nasal passage, said coupling portion being coupled to said tube; and
   an overflow coupled to said tip, said overflow extending rearwardly from said coupling portion of said tip and away from said nozzle, said overflow and said nozzle each being in fluid communication with said tip tube.

2. The assembly according to claim 1 further comprising said pump being positioned within an interior of said housing proximate a top side of an outer wall of said housing.

3. The assembly according to claim 1 further comprising:
   said medication reservoir being positioned within an interior of said housing proximate a bottom side of an outer wall of said housing; and
   said medication reservoir being in fluid communication with said pump wherein said pump draws the medication outwardly from said medication reservoir.

4. The assembly according to claim 1 further comprising:
   said port being coupled to a top side of an outer wall of said housing; and
   said port being fluidly coupled to said pump.

5. The assembly according to claim 1 further comprising said port being one of a pair of said ports.

6. The assembly according to claim 5 further comprising:
   a vacuum one of said pair of ports being positioned proximate a first lateral side of said outer wall of said housing; and said vacuum port being fluidly coupled to an inlet of said pump.

7. The assembly according to claim 5 further comprising:
a spray one of said pair of ports being positioned proximate a second lateral side of said outer wall of said housing; and
said spray port being fluidly coupled to an outlet of said pump.

8. The assembly according to claim 1 further comprising:
said actuator being centrally coupled to a front side of an outer wall of said housing proximate a bottom side of said outer wall of said housing; and
said actuator being electrically coupled to said pump.

9. The assembly according to claim 1 further comprising said control being coupled to a front side of an outer wall of said housing.

10. The assembly according to claim 1 further comprising said control being one of a pair of said controls.

11. The assembly according to claim 10 further comprising:
a vacuum one of said pair of controls being positioned proximate an intersection of a bottom side and a first lateral side of an outer wall of said housing; and
said vacuum control being operationally coupled to an inlet of said pump wherein said vacuum control adjusts a vacuum pressure of said inlet of said pump.

12. The assembly according to claim 10 further comprising:
a spray one of said pair of controls being positioned proximate an intersection of a bottom side and a second lateral side of an outer wall of said housing; and
said spray control being operationally coupled to an outlet of said pump wherein said spray control adjusts a spray pressure of said outlet of said pump.

13. The assembly according to claim 1 further comprising said meter being centrally coupled to a front side of an outer wall of said housing proximate a top side of said outer wall of said housing.

14. The assembly according to claim 1 further comprising:
said tube being one of a pair of said tubes;
a first end of a vacuum one of said pair of tubes being fluidly coupled to a vacuum port; and
a first end of a spray one of said pair of tubes being fluidly coupled to a spray port.

15. The assembly according to claim 1 further comprising:
said canister being one of a pair of said canisters;
a vacuum one of said pair of canisters being fluidly coupled to a second end of a vacuum tube; and
a spray one of said pair of canisters being fluidly coupled to a second end of a spray tube wherein said pump delivers the medication into said spray canister.

16. The assembly according to claim 1 further comprising:
said tip being fluidly coupled to a second end of said tip tube; and
a first end of said tip tube being selectively fluidly coupled to a selected one of a vacuum canister or a spray canister wherein said tip produces a vacuum pressure or a spray pressure.

17. The assembly according to claim 1 further comprising:
a power supply coupled to said housing;
said power supply being electrically coupled to said actuator; and
said power supply comprising at least one battery.

18. A vacuum assembly for clearing a user's nasal passage, said assembly comprising:
a housing configured to be positioned proximate the user;
a pump coupled to said housing, said pump being positioned within an interior of said housing proximate a top side of an outer wall of said housing;
a medication reservoir coupled to said pump wherein said medication reservoir is configured to selectively receive a medication, said medication reservoir being positioned within an interior of said housing proximate a bottom side of said outer wall of said housing, said medication reservoir being in fluid communication with said pump wherein said pump draws the medication outwardly from said medication reservoir;
a port coupled to said top side of said outer wall of said housing, said port being fluidly coupled to said pump, said port being one of a pair of said ports;
a vacuum one of said pair of ports being positioned proximate a first lateral side of said outer wall of said housing, said vacuum port being fluidly coupled to an inlet of said pump;
a spray one of said pair of ports being positioned proximate a second lateral side of said outer wall of said housing, said spray port being fluidly coupled to said outlet of said pump;
an actuator being centrally coupled to a front side of said outer wall of said housing proximate said bottom side of said outer wall of said housing, said actuator being electrically coupled to said pump;
a control coupled to said front side of said outer wall of said housing, said control being one of a pair of said controls;
a vacuum one of said pair of controls being positioned proximate an intersection of said bottom side and said first lateral side of said outer wall of said housing, said vacuum control being operationally coupled to said inlet of said pump wherein said vacuum control adjusts a vacuum pressure of said inlet of said pump;
a spray one of said pair of controls being positioned proximate an intersection of said bottom side and said second lateral side of said outer wall of said housing, said spray control being operationally coupled to said outlet of said pump wherein said spray control adjusts a spray pressure of said outlet of said pump;
a meter centrally coupled to said front side of said outer wall of said housing proximate said top side of said outer wall of said housing, said meter being operationally coupled to said pump wherein said meter displays a pressure of said pump;
a tube operationally coupled to said port, said tube being one of a pair of said tubes;
a first end of a vacuum one of said pair of tubes being fluidly coupled to said vacuum port;
a first end of a spray one of said pair of tubes being fluidly coupled to said spray port;
a canister operationally coupled to said tube, said canister being one of a pair of said canisters;
a vacuum one of said pair of canisters being fluidly coupled to a second end of said vacuum tube;
a spray one of said pair of canisters being fluidly coupled to a second end of said spray tube wherein said pump delivers the medication into said spray canister;
a tip fluidly coupled to a second end of a tip tube, a first end of said tip tube being selectively fluidly coupled to a selected one of said vacuum canister or said spray canister wherein said tip produces a vacuum pressure or a spray pressure, said tip being selectively inserted into the user's nasal passage wherein the user's nasal passage is cleared when said tip tube is fluidly coupled to said vacuum canister, said tip delivering the medication into the user's nasal passage when said tip tube is fluidly coupled to said spray canister;

an overflow coupled to said tip, said overflow extending rearwardly from a coupling portion of said tip and away from a nozzle of said tip, said overflow and said nozzle each being in fluid communication with said tip tube; and a power supply coupled to said housing, said power supply being electrically coupled to said actuator, said power supply comprising at least one battery.

* * * * *